(12) United States Patent
Mitra et al.

(10) Patent No.: US 9,975,841 B2
(45) Date of Patent: May 22, 2018

(54) LARGE MOLECULE AND POLYMER FLAME RETARDANTS

(71) Applicant: MegaMatter Inc., San Luis Obispo, CA (US)

(72) Inventors: Roopak Mitra, San Luis Obispo, CA (US); Haydn Mitchell, San Luis Obispo, CA (US); Harrison Ewan, San Luis Obispo, CA (US); Arlin Krigel, San Luis Obispo, CA (US); Philip Costanzo, San Luis Obispo, CA (US)

(73) Assignee: MegaMatter, Inc., San Luis Obispo, CA (US)

( * ) Notice: Subject to any disclaimer, the term of this patent is extended or adjusted under 35 U.S.C. 154(b) by 278 days.

(21) Appl. No.: 14/716,545

(22) Filed: May 19, 2015

(65) Prior Publication Data
US 2015/0329513 A1   Nov. 19, 2015

Related U.S. Application Data

(60) Provisional application No. 62/000,269, filed on May 19, 2014, provisional application No. 62/105,524, filed on Jan. 20, 2015.

(51) Int. Cl.
| | | |
|---|---|---|
| C08F 34/02 | (2006.01) |
| C08G 63/02 | (2006.01) |
| C07H 23/00 | (2006.01) |
| C07D 307/60 | (2006.01) |
| C07D 307/77 | (2006.01) |
| C07C 63/00 | (2006.01) |
| C07C 61/39 | (2006.01) |
| C07D 307/00 | (2006.01) |
| C07D 307/93 | (2006.01) |
| C08G 63/00 | (2006.01) |
| C08L 5/00 | (2006.01) |
| C08L 93/04 | (2006.01) |
| C08L 99/00 | (2006.01) |
| C07D 307/83 | (2006.01) |
| C08G 63/06 | (2006.01) |

(52) U.S. Cl.
CPC ............ *C07C 61/39* (2013.01); *C07D 307/00* (2013.01); *C07D 307/60* (2013.01); *C07D 307/77* (2013.01); *C07D 307/83* (2013.01); *C07D 307/93* (2013.01); *C08G 63/00* (2013.01); *C08G 63/06* (2013.01); *C08L 5/00* (2013.01); *C08L 93/04* (2013.01); *C08L 99/00* (2013.01)

(58) Field of Classification Search
CPC ........ C07C 61/39; C08G 63/00; C08G 63/06; C07D 307/60; C07D 307/77; C07D 307/93; C07D 307/83; C07D 307/00; C08L 93/04; C08L 5/00; C08L 99/00
USPC .......... 526/271; 528/272; 536/121; 549/233, 549/234, 235, 240; 562/488
See application file for complete search history.

(56) References Cited

U.S. PATENT DOCUMENTS

| | | |
|---|---|---|
| 5,972,094 A | 10/1999 | Bates et al. |
| 8,222,190 B2 | 7/2012 | Zhamu et al. |
| 2004/0044141 A1 | 4/2004 | McGrail et al. |
| 2004/0220311 A1* | 11/2004 | Dotson ................. C08K 5/098 524/394 |
| 2004/0256605 A1 | 12/2004 | Reinheimer et al. |
| 2005/0032966 A1 | 2/2005 | Meijer et al. |
| 2005/0176881 A1* | 8/2005 | Bheda ................. C08G 63/916 524/599 |
| 2013/0264509 A1 | 10/2013 | Shalev et al. |

FOREIGN PATENT DOCUMENTS

| | | |
|---|---|---|
| WO | WO 2000/029662 A1 | 5/2000 |
| WO | WO 2003/072871 A1 | 9/2003 |
| WO | 2015022262 A1 | 2/2015 |
| WO | 2015179426 A1 | 11/2015 |
| WO | 2017218547 A1 | 12/2017 |

OTHER PUBLICATIONS

International Search Report and Written Opinion for PCT/US2017/037272 dated Aug. 28, 2017.
International Search Report and Written Opinion for PCT/US2015/031615 dated Sep. 17, 2015.

* cited by examiner

*Primary Examiner* — William Cheung
(74) *Attorney, Agent, or Firm* — Pepper Hamilton LLP

(57) ABSTRACT

Disclosed herein are flame retardant compounds and polymer compositions containing these flame retardant compounds. The flame retardant compounds can be derived from biological sources and can include coordinated metal ions.

18 Claims, No Drawings

LARGE MOLECULE AND POLYMER FLAME RETARDANTS

CROSS-REFERENCE TO RELATED APPLICATIONS

This application claims priority to U.S. Provisional Application No. 62/000,269 filed May 19, 2014 and U.S. Provisional Application No. 62/105,524 filed Jan. 20, 2015, each of which is hereby incorporated by reference in its entirety.

GOVERNMENT INTERESTS

Not applicable

PARTIES TO A JOINT RESEARCH AGREEMENT

Not applicable

INCORPORATION BY REFERENCE OF MATERIAL SUBMITTED ON A COMPACT DISC

Not applicable

BACKGROUND

Fireproofing technology is a major industry. Flame retardants are in a transition state in which older flame retardants are being banned and subsequently phased out due to growing concerns over the health and environmental impacts of chemical agents.

Many metallo-organic compounds have been shown to have flame retardant properties. Various metallo-organic compounds that have strong tunable flame retardant properties including, but not limited to, a robust char layer, intumescence, and carbon dioxide production. The metallo-organic compounds described within are novel in their synthetic pathway, chemical structure, their coating process, and their mechanical action as an additive flame retardant.

SUMMARY OF THE INVENTION

Embodiments are directed to a flame retardant compound of Formula I:

$$R^1\text{—}X\text{—}R^2 \qquad \text{I}$$

wherein X is aryl, alkaryl, heteroaryl, cycloalkyl, heterocycloalkyl, cycloalkenyl, heterocycloalkenyl, or combinations thereof; $R^1$ is a saturated aliphatic chain, an unsaturated aliphatic chain, a branched aliphatic chain, an unbranched aliphatic chain, a substituted aliphatic chain, an unsubstituted aliphatic chain, or any combination thereof and $R^2$ is an oxidizable group selected from carboxyl, anhydride, amide, nitro, nitroso, thioester, and combinations thereof. In some embodiments, $R^1$ may be an aliphatic chain having about 3 to about 22 carbon atoms. In certain embodiments, $R^2$ may be a carboxyl, an anhydride, an amide, or any combination thereof. In particular embodiments, X may be aryl, alkaryl, heteroaryl, cycloalkyl, heterocycloalkyl, or any combination thereof. In various embodiments, the compound may be a rosin compound, a polyanhydride compound, or combinations thereof, and in some embodiments, the compound may further include a metal ion coordinated to one or more $R^2$.

Other embodiments are directed to a flame retardant compound of Formula II:

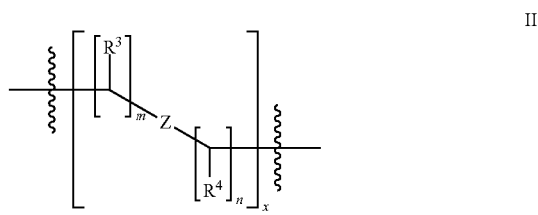

wherein m is an integer from 1 to 20; n is an integer from 1 to 20; x is an integer from 1 to 10,000; each $R^3$ is individually a saturated aliphatic chain, an unsaturated aliphatic chain, a branched aliphatic chain, an unbranched aliphatic chain, a substituted aliphatic chain, an unsubstituted aliphatic chain, or any combination thereof; each $R^4$ is individually an oxidizable group selected from a carboxyl, an anhydride, an amide, a nitro group, a nitroso group, a thioester group, and any combination thereof; and Z is 0-20 atoms of carbon, oxygen, sulfur, phosphorous, and any combination thereof. In some embodiments, the compound may be a rosin compound, a polyanhydride compound, or combinations thereof. In particular embodiments, the compound may be a bio-sourced material, and in some embodiments, the bio-sourced material may be a polysaccharide with associated or chemically bonded proteins having one or more ether, alcohol, epoxide, ketone, aldehyde, carboxylic acid, ester, acid chloride, amine, amide, imine, thioester, sulfone, thiol, sulfide, phosphate, phosphate ester, acyl phosphate, alkyl, alkene, alkyne, or combinations thereof. In some embodiments, the compound may further include a metal ion coordinated to one or more $R^4$. In certain embodiments, the compound may be selected from:

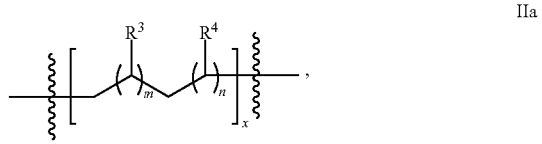

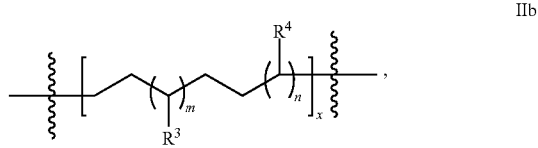

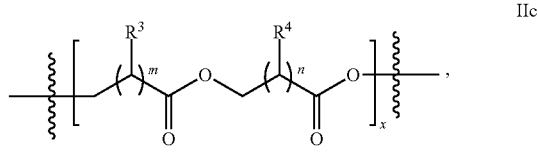

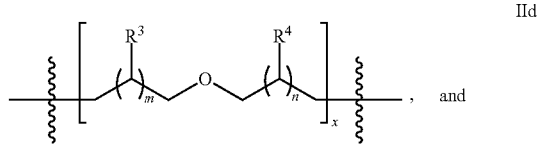

-continued

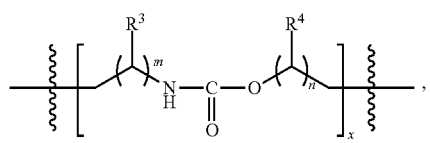

IIe and in certain embodiments, these compounds may further include a metal ion coordinated to one or more $R^4$.

Certain embodiments are directed to a flame retardant compound of formula

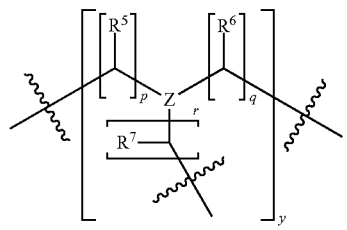

III wherein p is an integer from 1 to 20; q is an integer from 1 to 20; r is an integer from 1 to 20; y is an integer from 1 to 10,000; each $R^5$, $R^6$, and $R^7$ is individually an aliphatic chain selected from a saturated aliphatic chain, an unsaturated aliphatic chain, a branched aliphatic chain, an unbranched aliphatic chain, a substituted aliphatic chain, an unsubstituted aliphatic chain, or any combination thereof; at least one of $R^5$, $R^6$, and $R^7$ is individually an oxidizable functional group selected from a carboxyl, an anhydride, an amide, a nitro group, a nitroso group, a thioester group, and any combination thereof and Z is 0-20 atoms of carbon, oxygen, sulfur, phosphorous, and any combination thereof. In certain embodiments, the compound may be a bio-sourced material, and in various embodiments, bio-sourced material may be a polysaccharide with associated or chemically bonded proteins having one or more ether, alcohol, epoxide, ketone, aldehyde, carboxylic acid, ester, acid chloride, amine, amide, imine, thioester, sulfone, thiol, sulfide, phosphate, phosphate ester, acyl phosphate, alkyl, alkene, alkyne, or combinations thereof. In some embodiments, the compounds may further include a metal ion coordinated to at least one of $R^5$, $R^6$, and $R^7$ containing an oxidizable group.

Particular embodiments are directed to a compound selected from:

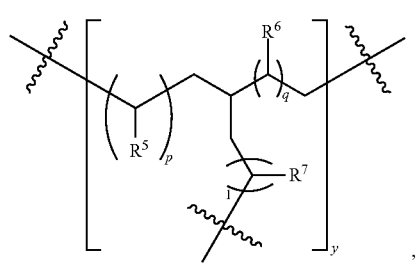

IIIa

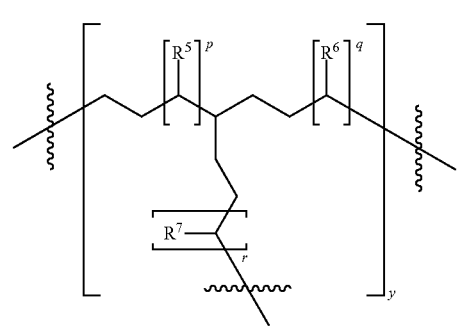

IIIb

, and

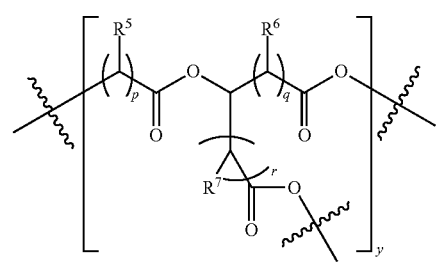

IIIc wherein $R^5$, $R^6$, $R^7$, p, q, and r are as described above. In some embodiments, these compounds may further include a metal ion coordinated to at least one of $R^5$, $R^6$, and $R^7$ containing an oxidizable group.

Various embodiments are directed to a flame retardant compound of Formula IV:

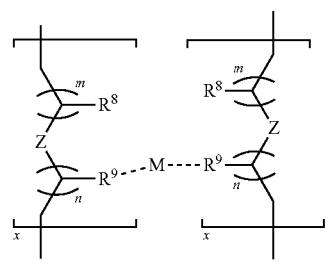

IV wherein m is an integer from 1 to 20; n is an integer from 1 to 20; x is an integer from 1 to 10,000; each $R^8$ is individually a saturated aliphatic chain, an unsaturated aliphatic chain, a branched aliphatic chain, an unbranched aliphatic chain, a substituted aliphatic chain, an unsubstituted aliphatic chain, or any combination thereof; each $R^9$ is individually an oxidizable group selected from carboxyl, anhydride, amide, nitro, nitroso, thioester, and combinations thereof; Z is 0-20 atoms of carbon, oxygen, sulfur, phosphorous, and any combination thereof; and M is a metal ion selected from Fe, Al, Si, Ti, Zr, Hf, V, Nb, Ta, Cr, Mn, Mo, W, Re, Co, Ni, Cu, Group III metals, and any combination thereof. In some embodiments, the compound may be a bio-sourced material, and in particular embodiments, the bio-sourced material may be a polysaccharide with associated or chemically bonded proteins having one or more ether, alcohol, epoxide, ketone, aldehyde, carboxylic acid, ester, acid chloride, amine, amide, imine, thioester, sulfone, thiol, sulfide, phosphate, phosphate ester, acyl phosphate, alkyl, alkene, alkyne, or combinations thereof.

Some embodiments are directed to a method of making a flame retardant compound, the method including the steps of combining a compound having an oxidizable group and a metal containing compound to form a reaction mixture; and mixing the reaction mixture. In various embodiments, the metal containing compound may be aluminum sulfate, aluminum oxalate, copper sulfate, magnesium sulfate, manganese sulfate, zinc sulfate, manganese oxalate, zinc oxalate, aluminum phosphate, or combinations thereof. In some embodiments, the method may further include the step of combining a base with the compound having an oxidizable group and the metal containing compound before or during mixing. In certain embodiments, the reaction mixture may further include a solvent. In certain embodiments, the method may further include the step of heating the reaction mixture to a temperature of about 50° C. to about 110° C.

Other embodiments are directed to a method of making a flame retardant including the steps of isolating a bio-based material having one or more ether, alcohol, epoxide, ketone, aldehyde, carboxylic acid, ester, acid chloride, amine, amide, imine, thioester, sulfone, thiol, sulfide, phosphate, phosphate ester, acyl phosphate, alkyl, alkene, alkyne, or combinations thereof from a biological sample; and combining the bio-based material with a metal in a solvent. In some embodiments, the polysaccharide may be mucilage isolated from a plant, and in particular embodiments, the polysaccharide may be mucilage isolated from one or more flax seeds. In various embodiments, the metal may be aluminum, and in some embodiments, metal may be an aluminum sulfate. Certain embodiments include the step of adding one or more additives to the composition.

DESCRIPTION OF DRAWINGS

Not Applicable

DETAILED DESCRIPTION

Before the present compositions and methods are described, it is to be understood that they are not limited to the particular compositions, methodologies or protocols described, as these may vary. It is also to be understood that the terminology used in the description is for the purpose of describing the particular versions or embodiments only, and is not intended to limit their scope which will be limited only by the appended claims.

It must also be noted that as used herein and in the appended claims, the singular forms "a", "an", and "the" include plural reference unless the context clearly dictates otherwise. Unless defined otherwise, all technical and scientific terms used herein have the same meanings as commonly understood by one of ordinary skill in the art. Although any methods and materials similar or equivalent to those described herein can be used in the practice or testing of embodiments disclosed, the preferred methods, devices, and materials are now described.

"Optional" or "optionally" means that the subsequently described event or circumstance may or may not occur, and that the description includes instances where the event occurs and instances where it does not.

"Substantially no" means that the subsequently described event may occur at most about less than 10% of the time or the subsequently described component may be at most about less than 10% of the total composition, in some embodiments, and in others, at most about less than 5%, and in still others at most about less than 1%.

The term "alkyl" or "alkyl group" refers to a branched or unbranched hydrocarbon or group of 1 to 20 carbon atoms, such as but not limited to methyl, ethyl, n-propyl, isopropyl, n-butyl, isobutyl, t-butyl, octyl, decyl, tetradecyl, hexadecyl, eicosyl, tetracosyl and the like. "Cycloalkyl" or "cycloalkyl groups" are branched or unbranched hydrocarbons in which all or some of the carbons are arranged in a ring such as but not limited to cyclopentyl, cyclohexyl, methylcyclohexyl and the like. The term "lower alkyl" includes an alkyl group of 1 to 10 carbon atoms.

The terms "flame retardant," "flame resistant," "fire resistant," or "fire resistance," as used herein, means that the composition exhibits a limiting oxygen index (LOI) of at least 27. "Flame retardant," "flame resistant," "fire resistant," or "fire resistance," may also be tested by measuring the after-burning time in accordance with the UL test (Subject 94). In this test, the tested materials are given classifications of UL-94 V-0, UL-94 V-1 and UL-94 V-2 on the basis of the results obtained with the ten test specimens. Briefly, the criteria for each of these UL-94-V-classifications are as follows:

UL-94 V-0: the total flaming combustion for each specimen after removal of the ignition flame should not exceed 10 seconds and the total flaming combustion for 5 specimens should not exceed 50 seconds. None of the test specimens should release any drips which ignite absorbent cotton wool.

UL-94 V-1: the total flaming combustion for each specimen after removal of the ignition flame should not exceed 30 seconds and the total flaming combustion for 5 specimens should not exceed 250 seconds. None of the test specimens should release any drips which ignite absorbent cotton wool.

UL-94 V-2: the total flaming combustion for each specimen after removal of the ignition flame should not exceed 30 seconds and the total flaming combustion for 5 specimens should not exceed 250 seconds. Test specimens may release flaming particles, which ignite absorbent cotton wool.

Fire resistance may also be tested by measuring after-burning time. These test methods provide a laboratory test procedure for measuring and comparing the surface flammability of materials when exposed to a prescribed level of radiant heat energy to measure the surface flammability of materials when exposed to fire. The test is conducted using small specimens that are representative, to the extent possible, of the material or assembly being evaluated. The rate at which flames travel along surfaces depends upon the physical and thermal properties of the material, product or assembly under test, the specimen mounting method and orientation, the type and level of fire or heat exposure, the availability of air, and properties of the surrounding enclosure. If different test conditions are substituted or the end-use conditions are changed, it may not always be possible by or from this test to predict changes in the fire-test-response characteristics measured. Therefore, the results are valid only for the fire test exposure conditions described in this procedure.

"Molecular weight," as used herein, can be determined by relative viscosity ($\eta$rel) and/or gel permeation chromatography (GPC). "Relative viscosity" of a polymer is measured by dissolving a known quantity of polymer in a solvent and comparing the time it takes for this solution and the neat solvent to travel through a specially designed capillary (viscometer) at a constant temperature. Relative viscosity is a measurement that is indicative of the molecular weight of a polymer. It is also well known that a reduction in relative viscosity is indicative of a reduction in molecular weight, and reduction in molecular weight causes loss of mechanical properties such as strength and toughness. GPC provides information about the molecular weight and molecular weight distribution of a polymer. It is known that the molecular weight distribution of a polymer is important to properties such as thermo-oxidative stability (due to different amount of end groups), toughness, melt flow, and fire resistance, for example, low molecular weight polymers drip more when burned.

The term "bio-based", "bio-organic", "bio-sourced", or "biopolymer" includes the synthesis and production of material, small molecules, large molecules, or polymers based off naturally occurring substances, with monomers that are sourced from biological entities or synthetically designed. The term bio-based, bio-organic, bio-sourced, or biopolymer includes any material, small molecule, large molecule, or polymer extracted, harnessed, or is a byproduct of a biological entity including plants, animals, and microbes (i.e. flax seeds, shrimp, bacteria, and yeast). In some embodiments, the bio-based, bio-organic, bio-sourced, or biopolymer may be mucilage, which can be sourced from a number of plants; flax seeds, kelp, and cactus. Mucilage consists primarily of complex carbohydrates, proteins, carbohydrate and protein blends, and carbohydrates bonded or adhered to proteins.

The terms "film" and "coating" may be used interchangeably throughout this document. The word coating within this document is used as a noun and a verb. Coating as noun may be defined as a layer, which the thickness of may be varied, of a material on a surface or a material used to cover a surface. Coating as a verb, is the act of covering a surface with a material. The word film as a noun may be defined as a thin covering, coating, skin, or membrane.

Embodiments of the invention are directed to high molecular weight and polymeric flame retardant compounds, compositions containing these flame retardant compounds, methods for making and using these compounds, and articles of manufacture containing the high molecular weight and polymeric flame retardants. In some embodiments, the flame retardants may include saturated or unsaturated hydrocarbon covalently attached to heat reactive center containing one or more oxidizable groups. When combined with a base polymer, the hydrocarbon can interact with the base polymer attaching the flame retardant to the base polymer. The heat reactive center will typically have a more hydrophilic character causing the heat reactive center to remain on the outer surface of the base polymer. When fire or heat contact the polymer, oxidation of the oxidizable groups of the heat reactive center may remove oxygen from the area surrounding the polymer reducing burning of the polymer. In some embodiments, the heat reactive center may further include metal, which may be released when the heat reactive center is heated or burned further reducing burning of the polymer.

The term "oxidizable group" refers to chemical handles that include heteroatoms and lone pair electrons that are available for bonding. Examples of "oxidizable groups" include, but not limited to, ketones, carboxylic acids, aldehydes, carbonates, thiocarbonates, lactams, and lactones. The chemical handles bond with metal ion species creating an metallo-organic complex.

The high molecular weight flame retardants of various embodiments may typically include saturated or unsaturated hydrocarbon covalently attached to a heat reactive center that includes one or more oxidizable groups associated with a cyclic system including one or more aryl, alkaryl, heteroaryl, cycloalkyl, heterocycloalkyl, cycloalkenyl, heterocycloalkenyl, and combinations thereof. In some embodiments, such flame retardants may be of general Formula I:

$$R^1\text{—}X\text{—}R^2 \qquad \text{I}$$

where X is a cyclic system of one or more aryl, alkaryl, heteroaryl, cycloalkyl, heterocycloalkyl, cycloalkenyl, heterocycloalkenyl, and combinations thereof, $R^1$ is a hydrocarbon containing one or more saturated or unsaturated, branched or unbranched, substituted or unsubstituted aliphatic chains, and $R^2$ is one or more oxidizable functional groups such as, for example, a carboxyl, an anhydride, an amide, a nitro group, a nitroso group, a thioester group, and combinations thereof.

Each compound encompassed by Formula I may include one or more $R^1$, and each $R^1$ may include an aliphatic chain having about 3 to about 22 carbon atoms, about 4 to about 20 carbon atoms, about 5 to about 18 carbon atoms, about 6 to about 16 carbon atoms or any number of carbon atoms encompassed by these ranges. Each $R^1$ may be straight or branched, and in some embodiments, combinations of straight or branched aliphatic chains may be associated with the same compound of Formula I. In various embodiments, each $R^1$ may individually be saturated (i.e., having no double bonds) or unsaturated having 1 or more double bonds that can occur anywhere along the chain. In certain embodiments, $R^1$ may be an alpha olefin. In some embodiments, each $R^1$ may individually be unsubstituted. In other embodiments, each $R^1$ may individually be a substituted with one or more groups such as, but not limited to, alcohols (—OH), amines (—NH2), ethers (—CH2-O—CH2-), esters (—C(O)—O—CH2-), carboxylic acids (—C(O)OH), halogens (F, Cl, Br, I), sulfates (—SO3-2), phosphates (—PO4H2), and the like and combinations thereof.

The compounds encompassed by Formula I may include one or more $R^2$ moieties and each $R^2$ can be any oxidizable functional group known in the art. Examples of oxidizable groups that are encompassed by $R^2$ include, but are not limited to, carboxyl, anhydride, amide, nitro group, nitroso group, thioester group, and the like, and combinations thereof. In some embodiments, $R^2$ may be maleic anhydride.

X is not limited to any particular cyclic system. Examples of cyclic systems encompassed by X include monocyclic, bicyclic, polycyclic, aliphatic or aromatic ring systems that can include both aliphatic and aromatic elements. In some embodiments, such cyclic systems may include one or more heteroatoms. Examples of ring systems encompassed by X include, but are not limited to, benzene, acenaphthene, acenaphthylene, acenaphthoquinone, anthracene, benzocyclobutene, benzocyclobutadiene, benzanthrone, benz[a]anthracene, benzo[a]pyrene, benzo[e]pyrene, benzo[b]fluoranthene, perylene, benzo[ghi]perylene, benzo[j]fluoranthene, benzo[k]fluoranthene, chrysene, coronene, dibenz[a,h]anthracene, fluoranthene, fluorene, indeno[1,2,3-cd]pyrene, phenanthrene, pyrene, naphthalene, naphthanthrone, quinoline, isoquinonline, and the like. In some embodiments, such cyclic systems may include one or more bridged groups having 1 or more carbon atoms in the bridge. In certain embodiments, such bridged groups may include one or more functional groups, and in particular embodiments, one or more $R^2$ may be contained on a bridged group.

$R^1$ and $R^2$ can be positioned at any carbon of the X moiety. In certain embodiments, $R^1$ and $R^2$ can be positioned on opposite sides of the X moiety. For example, where X is naphthalene and $R^1$ is at the 1- or 2-position, $R^2$ may be at the 5- or 6-position. More complex cyclic systems may be similarly arranged with $R^1$ and $R^2$ being separated by at least 2 or more carbon atoms such that these substituents are on opposite sides of the molecule. In embodiments including more than one $R^1$, $R^2$, or multiple $R^1$'s and $R^2$'s, each $R^1$ and each R² may be grouped on opposite sides of the molecule. For example, where X is naphthalene and an R¹ is attached at the 1- and 2-positions, R² may be substituted at the 5- or 6-position or both the 5- and 6-position. In further embodiments, R¹ and R² may be on adjacent carbons of the X moiety.

In particular embodiments, the compounds of Formula I may be based on rosin compounds. Rosins or rosin compounds are well known abietyl compounds or hydrophenanthrene radical-containing materials, including but not limited to, tall oil rosin, tall oil fractions predominating in rosin acids containing at least about 50% by weight rosin acids; wood rosin; and gum rosin. Rosin acids are commonly mixtures of a wide variety of different isomers of monocarboxylic tricyclic rosin acids usually containing around 20 carbon atoms. The tricyclic rosin acids differ mainly in the position of the double bonds. Typically, the rosin is a mixture of substances comprising levopimaric acid, neoabietic acid, palustric acid, abietic acid, dehydroabietic acid, seco-dehydroabietic acid, tetrahydroabietic acid, dihydroabietic acid, pimaric acid, and isopimaric acid. The rosin acids derived from natural sources also include rosins, i.e. rosin mixtures, modified notably by polymerization, isomerization, disproportionation and hydrogenation. Rosins further encompass modified rosins that have been treated to produce hydrogenated rosins, formaldehyde-treated rosins, fumarated rosins, maleated rosins and derivatives of such rosins including, for example, rosin esters, rosin amines, rosin amides, rosin alcohols, rosin-alkylene oxide adducts, and the like and combinations thereof. Rosin esters include reaction products of rosin and mono- and polyhydroxy alcohols such as methanol, ethanol, butanol, ethylene glycol, pentaerthritol, glycerol, and the like. Rosin amines include the reaction products from dehydrating the ammonium salt of rosin to the nitrile which is then reduced by hydrogen to the amine. Rosin amides are the reaction products of decomposing ammonium salts of rosin or reacting rosin with primary amines. Rosin alcohols include reduced rosin esters, and rosin-alkylene oxide adducts include the known reaction products of rosin and ethylene oxide, and the like.

In some embodiments, the compounds of Formula I may be polyanhydride compounds or polymers. A polyanhydride polymer is a polymer having at least some anhydride linkages between subunits of the polymer chain. More particularly, a polyanhydride polymer includes polyester or polyether subunits or blocks joined by anhydride linkages, and this polymer is also identified herein as a mixed polyester/polyanhydride or polyether/polyanhydride polymer. This polyanhydride polymer may also contain other polymer subunits or blocks, forming block copolymers whose blocks are linked by anhydride linkages. The composition of such polyanhydride co-polymers may be expressed in terms of relative weight percent of the two polymer blocks making up the block co-polymer. In some embodiments, a preferred group of polyanhydride compounds includes polymers that are comprised of compounds containing at least one free carboxylic acid group, and at least one alcohol group, carboxylic acid or amine group available for reactions which can self polymerize or co-polymerize with carboxylic acid, alcohol or amine groups or bis(acyl) chlorides.

Particular examples of compounds of Formula I include, but are not limited to, the compounds presented in Table I.

TABLE I

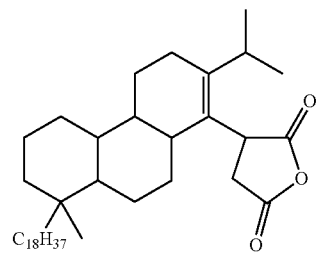

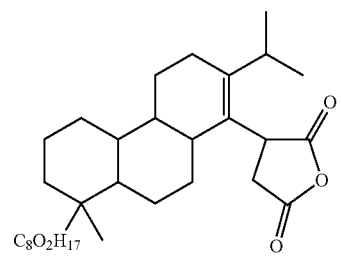

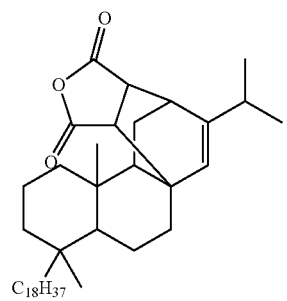

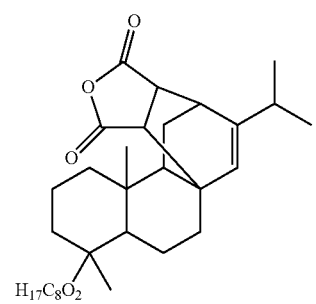

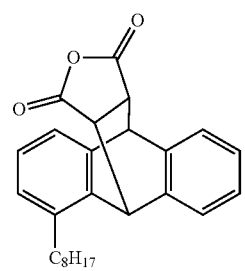

TABLE I-continued

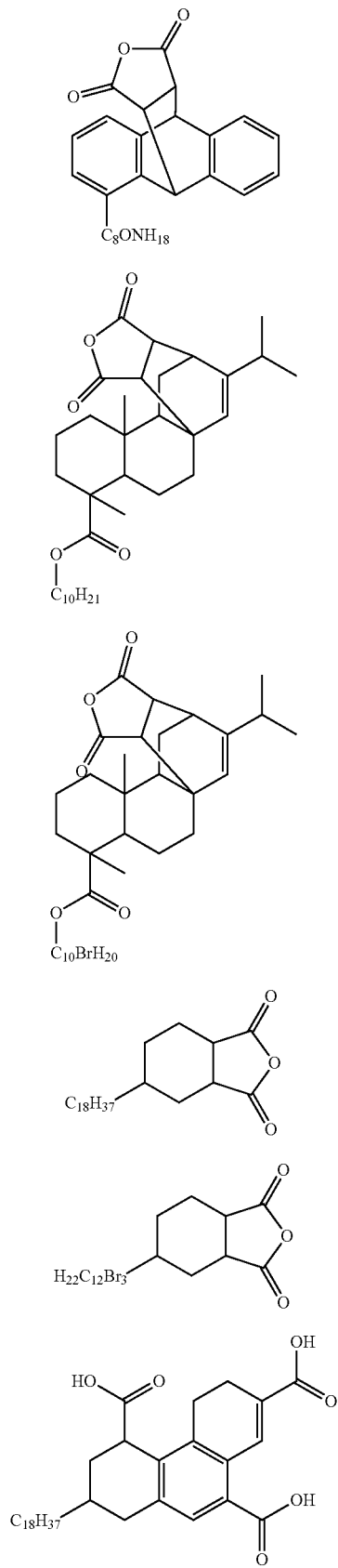

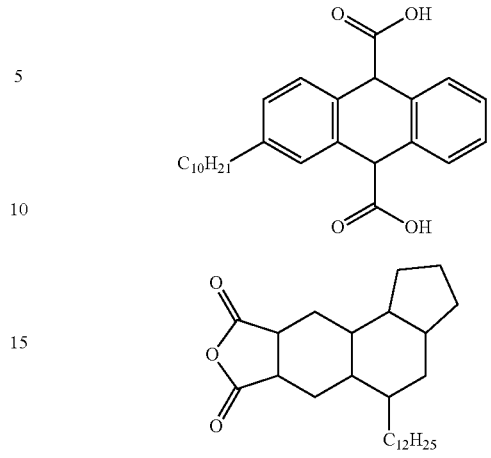

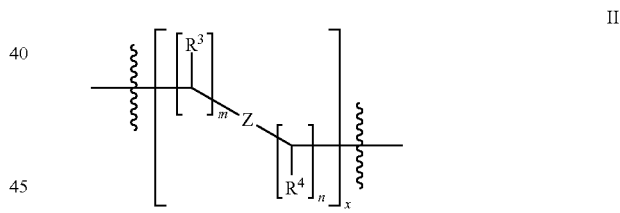

Other embodiments are directed to polymeric flame retardant compounds. The polymers of such embodiments may include monomeric units containing an aliphatic hydrocarbon and other monomeric units containing oxidizable functional groups. These monomeric units may be arranged randomly, in which individual monomers are arranged in linear order such that neighboring monomeric units may be of the same or a different type, or in blocks, in which continuous chains of aliphatic hydrocarbon containing monomers are linked to continuous chains of oxidizable functional group containing monomers. Lastly, they may be ordered in a branched fashion with either the aliphatic hydrocarbon or oxidizable function group monomer as the branched segment. In some embodiments, the polymeric flame retardants may be of Formula II:

II wherein each $R^3$ is individually a hydrocarbon containing one or more saturated or unsaturated, branched or unbranched, substituted or unsubstituted aliphatic chains; each $R^4$ is individually one or more oxidizable groups such as, for example, a carboxyl, an anhydride, an amide, a nitro group, a nitroso group, a thioester group, and combinations thereof; m and n are each, individually, integers of 1 to 20, and x is an integer of 1 to 10,000, 1 to 1500, 1 to 1000, 1 to 750, 1 to 500, 1 to 250, 1 to 100, 1 to 75, 1 to 50, 1 to 25, 1 to 10, or any range or individual value encompassed by these example ranges; and Z is absent or 1-20 atoms of carbon, oxygen, sulfur, phosphorous, and the like and combinations thereof.

Each $R^3$ may include an aliphatic chain having about 3 to about 22 carbon atoms, about 4 to about 20 carbon atoms, about 5 to about 18 carbon atoms, about 6 to about 16 carbon atoms or any number of carbon atoms encompassed by these ranges. Each $R^3$ may be straight or branched, and in some embodiments, the polymeric flame retardants encompassed by Formula II may include combinations of $R^3$ that are straight and branched. In various embodiments, each $R^3$ may individually be saturated (i.e., having no double bonds) or unsaturated having 1 or more double bonds that can occur anywhere along the chain. In certain embodiments, $R^3$ may be an alpha olefin. In some embodiments, each $R^3$ may individually be unsubstituted. In other embodiments, each $R^3$ may individually be a substituted with one or more groups such as, but not limited to, alcohols (—OH), amines (—NH$_2$), ethers (—CH$_2$—O—CH$_2$—), esters (—C(O)—O—CH$_2$—), carboxylic acids (—C(O)OH), halogens (F, Cl, Br, I), sulfates (—SO$_3^{-2}$), phosphates (—PO$_4$H$_2$), and the like and combinations thereof.

Each $R^4$ can be any oxidizable group known in the art. Examples of oxadizable groups that are encompassed by $R^4$ include, but are not limited to, carboxyl, anhydride, amide, nitro group, nitroso group, thioester group, and the like and combinations thereof. In some embodiments, $R^4$ may be maleic anhydride.

The ratio of m and n can vary among embodiments. For example, in some embodiments the ratio of $R^3$ containing monomers to $R^4$ containing monomers may be about 1:1, about 2:1, about 3:1, about 4:1, about 6:1, about 10:1, about 15:1, about 20:1, about 1:2, about 1:3, about 1:4, about 1:6, about 1:10, about 1:15, about 1:20, or any ratio encompassed by these example ratios.

In some embodiments, Z in Formula II can be, one or more atoms such as carbon, oxygen, sulfur, phosphorous, and the like and combinations thereof. These intervening atoms may make up a polymer backbone having various features including for example, double bonds, ether groups, ester groups, urethane linkages, vinyl groups, styryl groups, acrylate groups, phenyl, phosphoester, and the like and combinations thereof. The overall polymer topology could include but is not limited to branched, hyperbranched, star, or comb topology. In some embodiments, Z may be absent and the carbon atoms containing $R^3$ and $R^4$ groups may be directly linked to each other. In some embodiments, the compounds of Formula II are polyanhydride compounds described above. In some embodiments, the compounds of Formula II are rosin compounds described above.

Examples of polymeric flame retardants encompassed by Formula II include compounds of Formulae IIa to IIe:

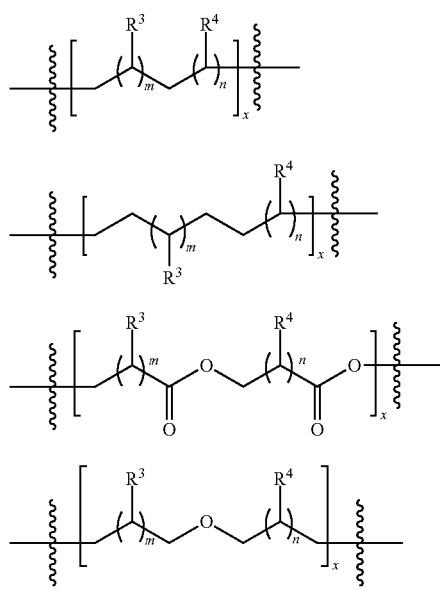

IIa

IIb

IIc

IId

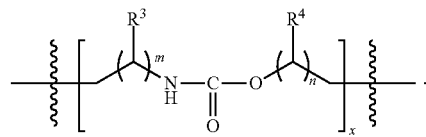

IIe where each $R^3$, $R^4$, m, n, and x are defined as described above with reference to Formula II.

Further non-limiting examples of compounds of Formula II include:

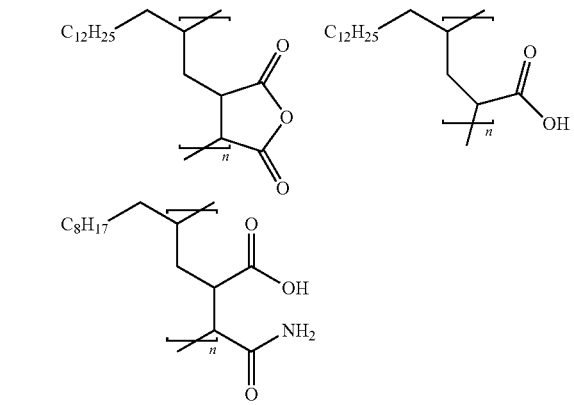

where each n is an integer of 1 to 10,000, 1 to 1500, 1 to 1000, 1 to 750, 1 to 500, 1 to 250, 1 to 100, 1 to 75, 1 to 50, 1 to 25, 1 to 10, or any range or individual value encompassed by these example ranges.

In some embodiments, the polymeric flame retardants may be of Formula III:

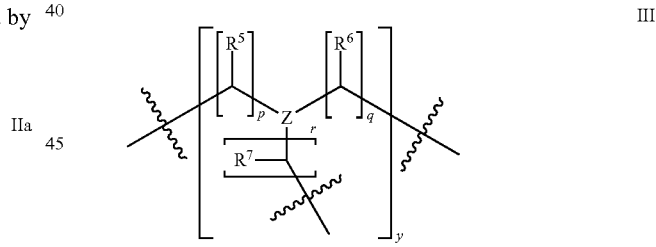

III where each $R^5$, $R^6$, and $R^7$ is individually an aliphatic chain or an oxidizable group; each Z can individually be 0-20 atoms of carbon, oxygen, sulfur, phosphorous, and the like and combinations thereof; each p, q, and r may individually be integers of 1 to 20; and y may be an integer of 1 to 10,000, 1 to 1500, 1 to 1000, 1 to 750, 1 to 500, 1 to 250, 1 to 100, 1 to 75, 1 to 50, 1 to 25, 1 to 10, or any range or individual value encompassed by these example ranges.

In embodiments in which one or more $R^5$, $R^6$, and $R^7$ is an aliphatic chain, the aliphatic chain may be saturated or unsaturated, branched or unbranched, substituted or unsubstituted aliphatic chain. In some embodiments, each $R^5$, $R^6$, and $R^7$ may individually be an aliphatic chain having about 3 to about 22 carbon atoms, about 4 to about 20 carbon atoms, about 5 to about 18 carbon atoms, about 6 to about 16 carbon atoms, or any number of carbon atoms encompassed by these ranges. In some embodiments, the polymeric flame retardants encompassed by Formula III may include combinations that are straight and branched. In various embodiments, each $R^5$, $R^6$, and $R^7$ may individually be saturated (i.e. having no double bonds) or unsaturated having 1 or more double bonds that can occur anywhere along the chain. In certain embodiments, each $R^5$, $R^6$, and $R^7$ may be an alpha olefin. In some embodiments, each $R^5$, $R^6$, and $R^7$ may individually be unsubstituted, and in other embodiments, each $R^5$, $R^6$, and $R^7$ may individually be a substituted with one or more groups such as, but not limited to, alcohols (—OH), amines (—$NH_2$), ethers (—$CH_2$—O—$CH_2$—), esters (—C(O)—O—$CH_2$—), carboxylic acids (—C(O)OH), halogens (F, Cl, Br, I), sulfates (—$SO_3^{-2}$), phosphates (—$PO_4H_2$), and the like and combinations thereof.

In embodiments in which one or more $R^5$, $R^6$, and $R^7$ is an oxidizable group, the oxidizable group may be carboxyl, anhydride, amide, nitro, nitroso, thioester, and the like and combinations thereof. In various embodiments, at least one of $R^5$, $R^6$, and $R^7$ is an aliphatic chain, and at least one of $R^5$, $R^6$, and $R^7$ is an oxidizable functional group. In some embodiments, the anhydride group may be maleic anhydride.

The ratio of p and q can vary among embodiments. For example, in some embodiments, the ratio of $R^5$ containing monomers to $R^6$ containing monomers may be about 1:1, about 2:1, about 3:1, about 4:1, about 6:1, about 10:1, about 15:1, about 20:1, about 1:2, about 1:3, about 1:4, about 1:6, about 1:10, about 1:15, about 1:20, or any ratio encompassed by these example ratios. The ratio of q and r can vary among embodiments. For example, in some embodiments, the ratio of $R^6$ containing monomers to $R^7$ containing monomers may be about 1:1, about 2:1, about 3:1, about 4:1, about 6:1, about 10:1, about 15:1, about 20:1, about 1:2, about 1:3, about 1:4, about 1:6, about 1:10, about 1:15, about 1:20, or any ratio encompassed by these example ratios. The ratio of p and r can vary among embodiments. For example, in some embodiments the ratio of $R^5$ containing monomers to $R^7$ containing monomers may be about 1:1, about 2:1, about 3:1, about 4:1, about 6:1, about 10:1, about 15:1, about 20:1, about 1:2, about 1:3, about 1:4, about 1:6, about 1:10, about 1:15, about 1:20, or any ratio encompassed by these example ratios.

In some embodiments, Z in Formula III can be, one or more atoms such as carbon, oxygen, sulfur, phosphorous, and the like and combinations thereof. These intervening atoms may make up a polymer backbone having various features including for example, double bonds, ether groups, ester groups, urethane linkages, vinyl groups, styryl groups, acrylate groups, phenyl, phosphoester, and the like and combinations thereof. The overall polymer topology could include but is not limited to branched, hyperbranched, star, or comb topology. In some embodiments, Z may be absent and the carbon atoms containing $R^5$, $R^6$, and $R^7$ groups may be directly linked to each other. In some embodiments, the compounds of Formula III are polyanhydride compounds described herein. In some embodiments, the compounds of Formula III are rosin compounds described herein.

Examples of polymeric flame retardants encompassed by Formula III include compounds of Formulae IIIa to IIIc:

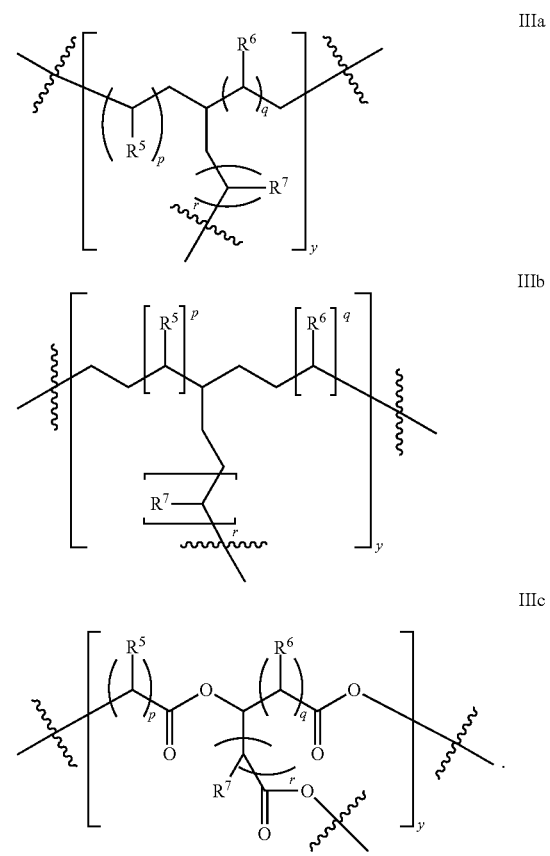

In some embodiments, compounds of Formulae I, II, or III may be present in co-ordination complex with metal ions. For example, the oxidizable groups may coordinate with a metal ion (M). The metal co-ordinated flame retardant compounds or polymers can be represented by the Formula IV:

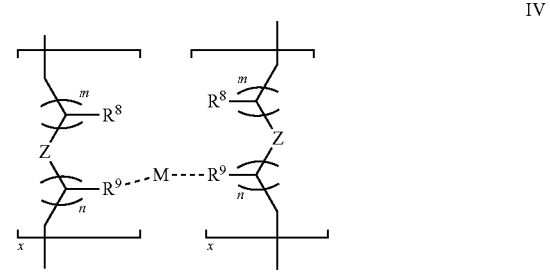

wherein each $R^8$ and $R^{8'}$ is a hydrocarbon containing one or more saturated or unsaturated, branched or unbranched, substituted or unsubstituted aliphatic chains; each $R^9$ and $R^{9'}$ is one or more oxidizable groups such as, for example, carboxyl, anhydride, amide, nitro, nitroso, thioester, and combinations thereof; m and n are each, individually, integers of 1 to 20; x is an integer of 1 to 10,000, 1 to 1500, 1 to 1000, 1 to 750, 1 to 500, 1 to 250, 1 to 100, 1 to 75, 1 to 50, 1 to 25, 1 to 10, or any range or individual value encompassed by these example ranges; and Z is 0-20 atoms of carbon, oxygen, sulfur, phosphorous, and the like and combinations thereof. The metal ion (M) of such embodiments may be selected from Fe, Al, Si, Ti, Zr, Hf, V, Nb, Ta, Cr, Mn, Mo, W, Re, Co, Ni, Cu, and combinations thereof. In some embodiments, Group III metals can also co-ordinate with oxygen atom of $R^9$ group.

Each $R^8$ and $R^{8'}$ may include an aliphatic chain having about 3 to about 22 carbon atoms, about 4 to about 20 carbon atoms, about 5 to about 18 carbon atoms, about 6 to about 16 carbon atoms or any number of carbon atoms encompassed by these ranges. Each $R^8$ and $R^{8'}$ may be straight or branched, and in some embodiments, the polymeric flame retardants encompassed by Formula IV may include combinations of $R^8$ and $R^{8'}$ that are straight and branched. In various embodiments, each $R^8$ and $R^{8'}$ may individually be saturated (i.e. having no double bonds) or unsaturated having 1 or more double bonds that can occur anywhere along the chain. In certain embodiments, $R^3$ may be an alpha olefin. In some embodiments, each $R^8$ and $R^{8'}$ may individually be unsubstituted. In other embodiments, each $R^8$ and $R^{8'}$ may individually be a substituted with one or more groups such as, but not limited to, alcohols (—OH), amines (—NH$_2$), ethers (—CH$_2$—O—CH$_2$—), esters (—C(O)—O—CH$_2$—), carboxylic acids (—C(O)OH), halogens (F, Cl, Br, I), sulfates (—SO$_3^{-2}$), phosphates (—PO$_4$H$_2$), and the like and combinations thereof.

Each $R^9$ and $R^{9'}$ can be any oxidizable group known in the art. Examples of oxadizable groups that are encompassed by $R^9$ and $R^{9'}$ include, but are not limited to, carboxyl, anhydride, amide, nitro, nitroso, thioester, and the like and combinations thereof. In some embodiments, each $R^9$ and $R^{9'}$ may be maleic anhydride.

The ratio of m and n can vary among embodiments. For example, in some embodiments the ratio of $R^8$ and $R^{8'}$ containing monomers to $R^9$ and $R^{9'}$ containing monomers may be about 1:1, about 2:1, about 3:1, about 4:1, about 6:1, about 10:1, about 15:1, about 20:1, about 1:2, about 1:3, about 1:4, about 1:6, about 1:10, about 1:15, about 1:20, or any ratio encompassed by these example ratios.

In some embodiments, Z in Formula IV can be, one or more atoms such as carbon, oxygen, sulfur, phosphorous, and the like and combinations thereof. These intervening atoms may make up a polymer backbone having various features including for example, double bonds, ether groups, ester groups, urethane linkages, vinyl groups, styryl groups, acrylate groups, phenyl, phosphoester, and the like and combinations thereof. The overall polymer topology could include but is not limited to branched, hyperbranched, star, or comb topology. In some embodiments, Z may be absent and the carbon atoms containing $R^8$ and $R^9$ groups may be directly linked to each other. In some embodiments, the compounds of Formula IV are polyanhydride compounds described above. In some embodiments, the compounds of Formula IV are rosin compounds described above.

In some embodiments, in the coordination complex of Formula IV, $R^9$ can be an anhydride group from the first compound and $R^{9'}$ can be another anhydride group from the second compound. In some embodiments, $R^9$ can be an anhydride group from the first compound and $R^{9'}$ can be a carboxyl group from the second compound. In some embodiments, $R^9$ can be an anhydride group from the first compound, and $R^{9'}$ can be an amide group from the second compound. In some embodiments, $R^9$ can be a carboxyl group from the first compound and $R^{9'}$ can be an amide group from the second compound. In some embodiments, $R^9$ can be a thioester group from the first compound, and $R^{9'}$ can be an amide group from the second compound.

In some embodiments, the coordination linkages may be intramolecular, and the $R^9$ and $R^{9'}$ groups in the coordination complex may be from the same compound. For example, $R^9$ can be an anhydride group and $R^{9'}$ can be another anhydride group from the same compound. Each $R^9$ and $R^{9'}$ may be on the same carbon atom, adjacent carbon atoms, or spaced 2-10 carbon atoms in length. Such compounds may be represented as follows:

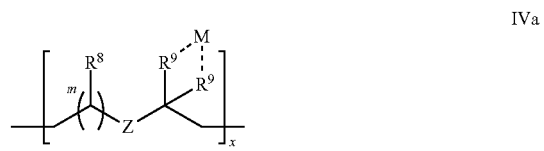

IVa

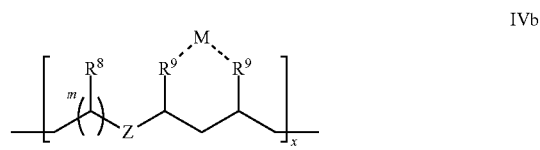

IVb

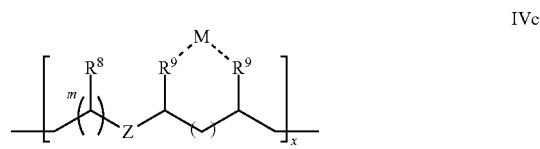

IVc

Non-limiting examples of metal-coordinated flame retardant compounds include the following:

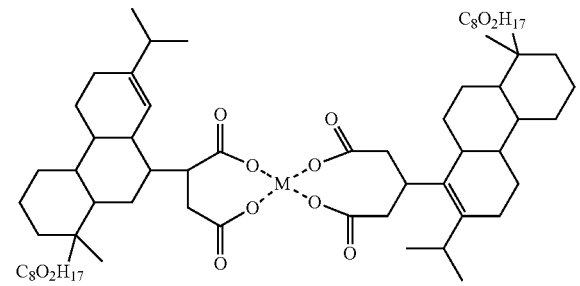

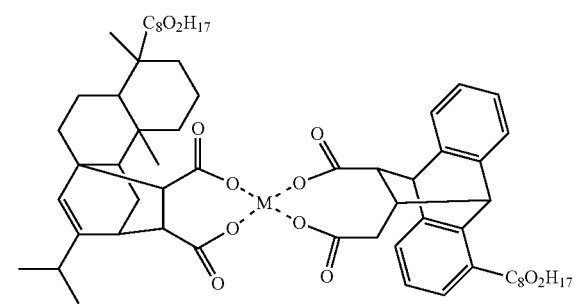

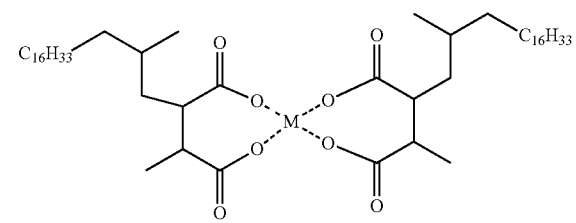

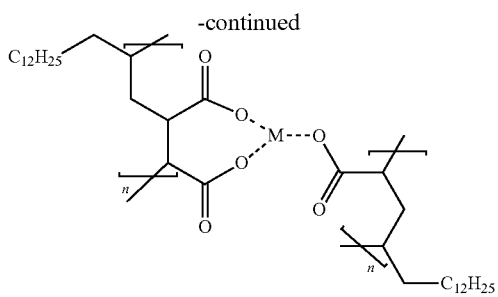

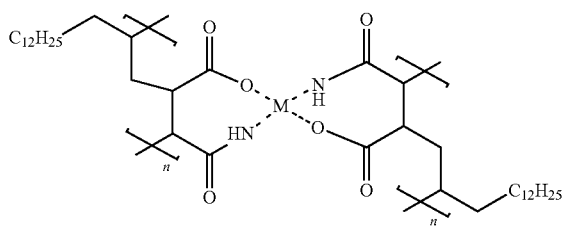

were each n is an integer of 1 to 10,000, 1 to 1500, 1 to 1000, 1 to 750, 1 to 500, 1 to 250, 1 to 100, 1 to 75, 1 to 50, 1 to 25, 1 to 10, or any range or individual value encompassed by these example ranges.

Additional embodiments include bio-organic flame retardants that fall within the formulae described above. In some embodiments, the bio-organic flame retardant blend may be derived from animal matter, and in other embodiments, the bio-organic flame retardant blend may be derived from plant matter. The bio-organic flame retardant blend includes, but is not limited to large and small molecules with oxidizable functional groups. These oxidizable groups may include, but are not limited to moieties with nitrogen, oxygen, sulfur, phosphorous, borate, and other elements in periodic groups 3-6. These elements may be bonded to include, for example, alcohols, ethers, amines, ketones, carboxylic acids, esters, and amides. In some embodiments, the bio-organic flame retardant blend is coordinated to metals and metal ion species. In some embodiments, the bio-organic flame retardant blend may be coated onto rigid surfaces in a continuous film, in either a regular or an irregular pattern. In some embodiments, the bio-organic flame retardant blend may be formed into pellets for incorporation into aggregate systems. In some embodiments, the bio-organic flame retardant blend maybe made from, for example, shrimp shells or plant mucilage, or combinations thereof.

In some embodiments, the bio-organic flame retardants may be provided in a blend of 1 to 100 different constituents. In some embodiments, three major component types that may constitute a bio-based flame retardant: the bio-organic flame retardant blend, one or more metal or metal ion species, and one or more additives. In some embodiments, the bio-organic flame retardant blend used may include a single material or chemical, a blend of organic materials, a blend of organic chemicals, or a blend of materials and chemicals. In some embodiments, the bio-organic flame retardant blend may use plant material include, for example, flowers, branches, leaves, thorns, and roots. In some embodiments, the plant material may be processed and the end product may have a collection of chemicals, tissues, and larger portions of the plant including, for example, fibers or bark and chemicals extracted from the tissues of the plant material, such as proteins and polysaccharides. More than one plant material may be used and processed together to make the bio-organic flame retardant blend.

In some embodiments, the bio-organic flame retardant blend may consist of biopolymers that make a binder or adhesive. In some embodiments, the bio-organic flame retardant blend may be a biopolymer with one or more repeating units of cyclic carbon structures with a range of 3 to 50 atoms in the cyclic structure. The cyclic structures may consist of carbon, hydrogen, oxygen, sulfur, phosphorous, nitrogen and other elements in periodic groups 3-6. The repeating cyclic units may have polar or nonpolar branched functional groups including, but not limited to, ethers, alcohols, epoxides, ketones, aldehydes, carboxylic acids, esters, acid chloride, amines, amides, imines, thioesters, sulfones, thiols, sulfides, phosphates, phosphate esters, acyl phosphate, alkyls, alkenes, alkynes, and combinations thereof. The polar or nonpolar branched functional groups may attach to any one of the atoms within each cyclic repeating unit. The polar or nonpolar branched functional groups may have various lengths, chemical structures, and topolgies. These biopolymers may be modified chemically or physically after they are obtained; they may be obtained via synthesis or a biological source.

In some embodiments, the bio-organic flame retardant blend may consist of one or more biopolymers. In some embodiments these biopolymers may include, but are not limited to polysaccharides, proteins, lipopolysaccharides, lipids, and organic materials. Polysaccharides may consist of, for example, glyceraldehyde, erythrose, threose, ribose, arabinose, xylose, lyxose, alfose, altrose, glucose, furanose, fructose, mannose, galactose, talose, aldose, and gulose. In some embodiments, the biopolymers may include mucilage, which consists primarily of complex carbohydrates, proteins, carbohydrate and protein blends, and carbohydrates bonded to proteins. The biopolymers may be chemically or physically modified, and may be processed further into a flame retardant. In some embodiments, the biopolymer may be pectin, which is a component of mucilage. In some embodiments, pectin extracted from the flax may consist mainly of D-galacturonic acid and arabonoxylan.

In some embodiments, oxidizable or polar functional groups in the bio-organic flame retardant blend or biopolymer may be combined with a metal or metal ion species including, but not limited to, Fe, Al, Si, Ti, Zr, Hf, V, Nb, Ta, Cr, Mn, Mo, W, Re, Co, Ni, Cu, Group III metals, and any combination thereof, in various mass ratios from 0.1:1 to 20:1 mucilage to metal or metal ion species. In some embodiments, the counter ion of the metal ion species may also be present in the final mixture. The metals, metal ion species, and/or counter ions may be added and may coordinate to the chemical moieties of the bio-organic flame retardant blend or the biopolymer. In some embodiments, the one or more metals, metal ion species, and/or counter ions may adhere to any portion of the bio-organic flame retardant blend or biopolymer.

The following bio-organic flame retardant blend compositions are non-limiting examples of structures that can be created by the processes described herein:

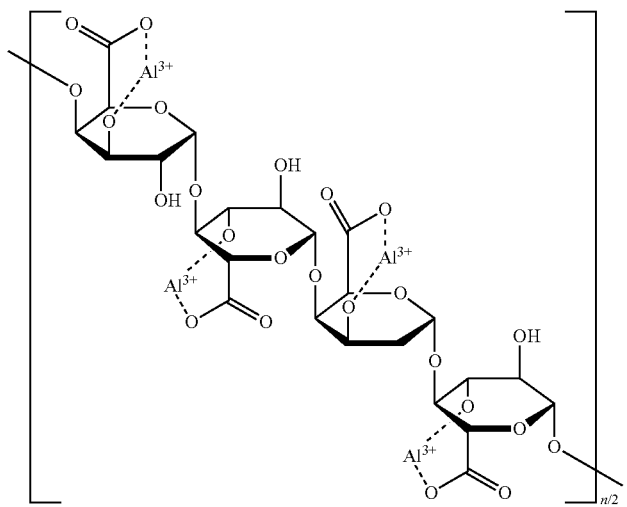
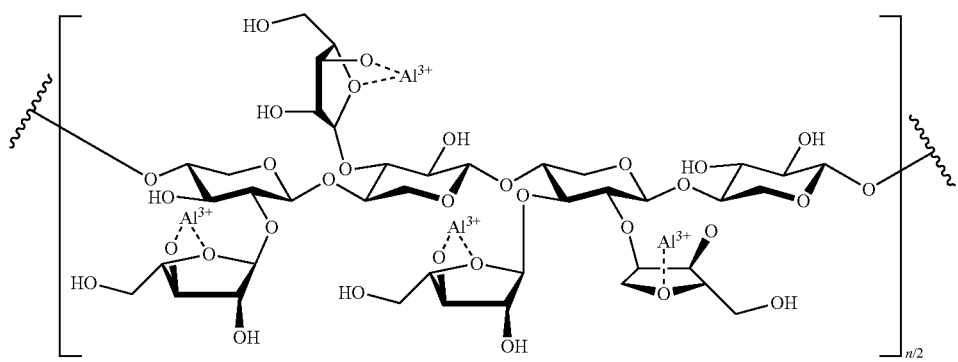
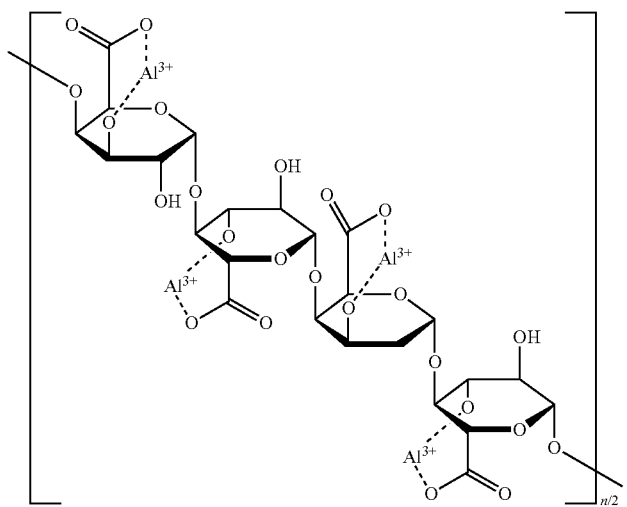

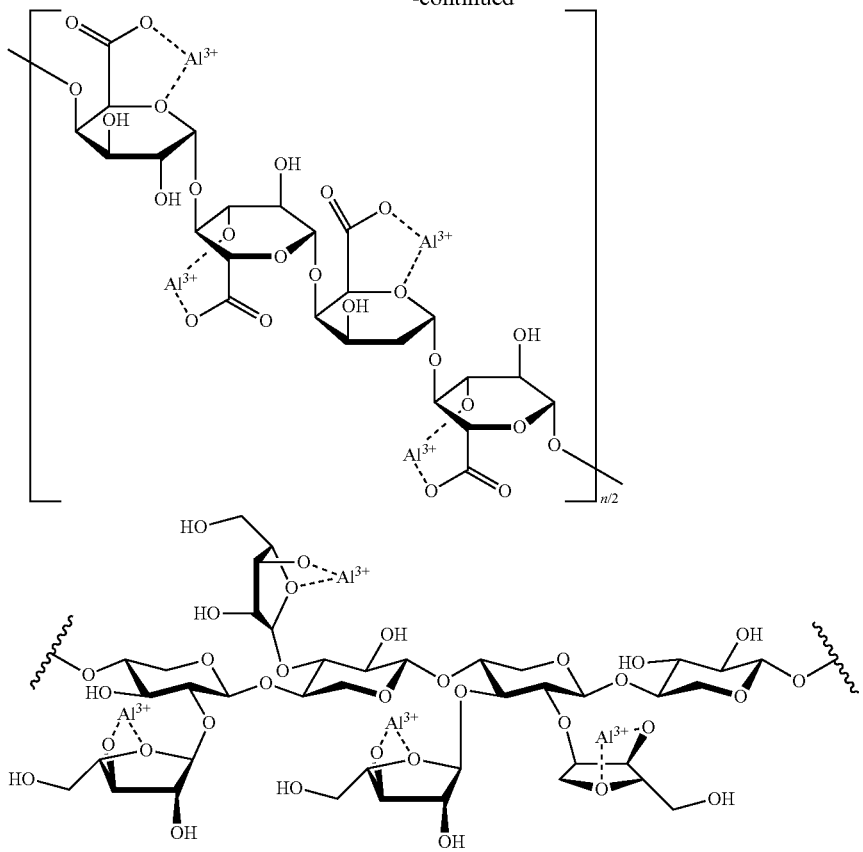

In some embodiments, one or more additives may be added to the mixture of the bio-organic flame retardant blend and metal or metal ion species. These additives may be included, for example, to alter the mixture's chemical or physical characteristics, or to improve flame retardancy. In some embodiments, additives may include, for example, glass fibers, Mg(OH2), glycerin, aluminum trihydrate, polyphosphates, silica fume, TiO2, sugar, glass fibers, bamboo fibers, and zinc oxide.

In some embodiments, the bio-organic flame retardant blend may consist of biopolymers that act as a binder or adhesive. In some embodiments, the bio-organic flame retardant blend may be a biopolymer with a repeating unit of cyclic carbon structures with a range of 3 to 50 atoms in the cyclic structure. The cyclic structure may consist of carbon, hydrogen, oxygen, sulfur, phosphorous, nitrogen and other elements in periodic groups 3-6. The repeating cyclic unit may have polar or nonpolar branched functional groups including, but not limited to, ethers, alcohols, epoxides, ketones, aldehydes, carboxylic acids, esters, acid chloride, amines, amides, imines, thioesters, sulfones, thiols, sulfides, phosphates, phosphate esters, acyl phosphate, alkyls, alkenes, alkynes, and combinations thereof. The polar or nonpolar branched functional groups may attach to any one of the atoms within each cyclic repeating unit. The branched units may have various lengths, chemical structures, and topologies.

In some embodiments, the bio-organic flame retardant blend may be extracted and/or harvested from a biological entity, or may be collected as the by-product of a natural or industrial process of the biological entity. The sources for the bio-organic flame retardant blend may include, for example, any plants, animals, or microbes. In some embodiments, the bio-organic flame retardant blends may be physically or chemically modified prior to their use in the production of a flame retardant.

In some embodiments, the bio-organic flame retardant blend may be extracted and/or harvested by methods including, for example, pulverizing, chopping, or cutting the raw materials. In some embodiments, the raw materials may then be further processed. In some embodiments, the processing may include, for example, boiling, soaking, and mixing with other chemicals.

In some embodiments, the bio-organic flame retardant blend may be extracted by pouring raw biological materials into a solvent, and raising the temperature to a boil. Then, the bio-organic flame retardant blend may be isolated from any waste or undesired byproducts of the process.

In some embodiments, the biological entities or raw biological materials may include, for example, seeds, succulents, bark of plants, leaves of plants, fruits and vegetables from plants, and water plants such as, for example, seaweed and kelp. In some embodiments, the seeds include, for example, flax seeds and chia seeds. In some embodiments, the succulents include, for example, cactus and aloe vera.

In some embodiments, the bio-organic flame retardant blend may be the mucilage obtained from biological entities. In particular embodiments, the bio-organic flame retardant blend includes mucilage extracted from flax seeds. Mucilage may be obtained from flax seeds by pouring either whole or processed flax seeds into a solvent and increasing the temperature until the mixture boils. The mucilage may then be suspended in the solvent. The flax seeds may be left in the mucilage solution, or may be strained and isolated from the mixture. In some embodiments, the solvent may be water. In some embodiments, the flax seeds may be soaked in cold water to extract the organic material needed to produce one or more components of the bio-organic flame retardant blend. Once the solution is thick with mucilage, the flax seeds may be strained from the solution. In some embodiments, whole or crushed flax seeds may be left in the solution. In some embodiments, the mucilage may include materials and chemicals added during the mucilage isolation process. These materials and chemicals may include, for example, glycerin, glass fibers, propylene glycol, gelatin, and oils. In other embodiments, the mucilage may be chemically or physically modified after isolation, but before the subsequent addition of chemicals to create the flame retardant. In some embodiments, the mucilage may be added to the metal or metal ion species in a 1:1 ratio by weight. In some embodiments, the metal or metal ion species may be aluminum sulfate.

In some embodiments, the bio-organic flame retardant blend may be combined with metal or metal ion species. The bio-organic flame retardant blend may be in a solvent, to which the metal or metal ion species may be added. In some embodiments, the resulting mixture is heated and solvent is driven off to create solution of 0.1 wt. % solids to 99.9 wt. % solids. In some embodiments, the bio-organic flame retardant blend retrieved from this solution may be added to metallic species including, for example, Fe, Al, Si, Ti, Zr, Hf, V, Nb, Ta, Cr, Mn, Mo, W, Re, Co, Ni, Cu, Group III metals, and any combination thereof, in various mass ratios from 0.1:1 to 20:1 mucilage to metal ion species to create a flame retardant.

Further embodiments are directed to methods for making flame retardant compounds and polymers. In some embodiments, the method involves combining a compound having one or more oxidizable groups and a metal compound to form a reaction mixture and mixing the reaction mixture. In some embodiments, combining may be carried out by dry mixing the reaction mixture, and in other embodiments, combining may be carried out by mixing the reaction mixture with water or another solvent. Although it is not necessary to heat the reaction mixture during mixing, in some embodiments, the method may include heating the reaction mixture during mixing. In certain embodiments, the reaction mixture may further include a base, and combining may include combining a compound having one or more oxidizable groups, a base, and a metal compound to form a reaction mixture. In some embodiments, the reaction mixture may further include graphite, and in certain embodiments, the graphite may be expandable graphite. After combining the components of the reaction mixture and dry mixing or mixing in a water or a solvent, the flame retardant may be combined with a polymer or polymer mixture that can be processed and/or molded, or the flame retardant can be applied to the surface of a molded article.

Mixing can be carried out by any method using any apparatus known in the art. In particular embodiments, mixing may be carried out by high intensity mixing, for example, greater than about 30,000 revolutions per minute, greater than about 35,000 revolutions per minute, and up to about 50,000 revolutions per minute or about 25,000 to about 50,000 revolutions per minute or about 30,000 to about 40,000 revolutions per minute.

In embodiments in which the reaction mixture is heated, the heating temperature may be about 50° C. to about 110° C. In particular embodiments, heating may be effectuated by the by heat from the mixing apparatus or by kinetic energy created during heating. Mixing can be carried out for about 30 minutes to about 6 hours. In some embodiments, the mixing can be performed until the solvent in the reaction mixture is the solvent is driven off leaving a paste or a dry flame retardant. In other embodiments, solvent may be driven off by other known techniques, such as boiling, air drying under ambient conditions, drying under reduced atmosphere, lyophilizing, refluxing, rotary evaporation, and the like.

The compound having oxidizable groups can be any of the compounds described above including the rosin compounds, polymeric compounds, and bio-organic compounds. Non-limiting examples of oxidizable functional groups include carboxyl, anhydride, amide, nitro, nitroso, thioester, and the like and any combination thereof. In some embodiments, the compound or the polymer may be a polyanhydride compound, such as PA-18, a rosin compound, or compounds of Formulae I, II, or III described above. The base may be, for example, hydrazine, NaOH, ammonium hydroxide, KOH, and other hydroxides of alkali metals and alkaline earth metals. In some embodiments, the metal compound may be phosphates, sulfates, carbonates, oxalates, and chlorides of Fe, Al, Si, Ti, Zr, Hf, V, Nb, Ta, Cr, Mn, Mo, W, Re, Co, Ni, Cu, Group III metals, and any combination thereof. In some embodiments, the metal compound may be aluminum sulfate.

Additional embodiments are directed to polymer compositions containing any of the flame retardants described above or combinations thereof blended with thermoplastic resins. Generally, the amount of the polymeric flame retardant (with or without flame retardant enhancing agents) employed when blended with a thermoplastic resin is that amount required to effectively enhance the flame retardant properties of the thermoplastic resin upon molding compared with the flame retardant properties of the thermoplastic resin in the absence of the polymeric flame retardant. The thermoplastic resins may vary among embodiments. Examples of such resins include, but are not limited to, polyolefins, styrenic polymers, graft copolymers of styrene on rubber, polymers and copolymers derived from unsaturated amines, polycarbonates, polyurethanes, polyesters, polyacrylates, silicones, epoxy resins, urea-formaldehyde resins, melamine-formaldehyde resins, hydroxymethyl urea-formaldehyde resins, hydroxymethyl melamine-formaldehyde resins, natural polymers, such as natural rubber, cellulose, and the like.

The polymeric flame retardants of the invention may be provided in an amount of about 5% to about 95% by weight relative to the weight of the total composition. In some embodiments, the polymeric flame retardants may be about 30% to about 70% by weight, about 30% to about 60% by weight, about 30% to about 50% by weight, about 30% to about 40% by weight, and ranges between these values based on the total weight of the polymer composition. In particular example embodiments, the flame retardant compounds described above can be added to the selected polyurethane foam formulations at from about 2 to about 35 parts by weight, about 2 to about 30 parts by weight, about 2 to about 25 parts by weight, or about 2 to about 15 parts by weight of the blend per 100 parts by weight of the polyol in the formulation (percent by weight of polyol). In some embodiments, such formulations may be used in flexible and rigid polyurethane foams. The flame retardant compounds can be incorporated into the polyurethane using a variety of procedures including admixing the flame retardant with the polyol reagent prior to the polymerization reaction, or the two individual components may be introduced as separate streams to a foam machine mixing head.

The polymeric flame retardants may be incorporated into end-use applications differently depending upon the composition of the polymer system being modified. For example, if it is desired to flame retard a polymer, copolymer or blend that contains a limited number of polymer-bound cyclic anhydride groups, part of the available anhydride groups can be transformed into the polymeric flame retardants of the present invention by adding the hydrazido-functionalized flame retardant and allowing the polymeric flame retardant to form during compounding, molding or curing of the polymer system. This is referred to as preparing the polymeric flame retardant at a minimum effective use level.

In addition, compounds of the invention may be cured to form resins. A variety of curing agents including, for example, acid catalysts, peroxides, or any commercially available hardeners may be used for this process.

Resins manufactured from the compounds described above may be blended with other additives to further enhance the properties of the finished polymer. Examples of other additives that can be used in conjunction with the flame retardants described above include antioxidants, such as alkylated monophenols, alkylated hydroquinones, hydroxylated thiodiphenyl ethers, alkylidenebis(phenols), hindered phenolic benzyl compounds, acylaminophenols, esters of 3-(3,5-di-t-butyl-4-hydroxyphenyl)propionic acid, esters of 3-(5-t-butyl-4-hydroxy-3-methylphenyl)propionic acid, 3-(3,5-di-t-butyl-4-hydroxyphenyl)propionic acid amides; UV absorbers and light stabilizers, such as 2-(2,-hydroxyphenyl)-2H-benzotriazoles, 2-hydroxybenzophenones, benzylidene malonate esters, esters of substituted or unsubstituted benzoic acids, diphenyl acrylates, nickel chelates, oxalic acid diamides, hindered amine light stabilizers; and other additives including metal deactivators, phosphites and phosphonites, peroxide decomposers, fillers and reinforcing agents, plasticizers, lubricants, corrosion and rust inhibitors, emulsifiers, mold release agents, carbon black, pigments, fluorescent brighteners, additional organic and inorganic flame retardants, nondripping agents, melt flow improvers and antistatic agents.

In some embodiments, the flame retardants of embodiments described above may be used with, for example, acrylic systems to provide excellent coatings for articles of manufacture, such as appliances, kitchen cabinets, outdoor furniture, aluminum siding, and other metal products. The poly-functional epoxy and amine resins with flame retardants may be used as, for example, a powder coating for anti-corrosion or a high sheen decorative coating. Such coatings may be used in articles of manufacture such as, for example, washing machines, appliances, ships, bridges, pipelines, chemical plants, automobiles, farm implements, containers, floor surfaces, and the like. The flame retardant compounds with acrylate functional groups may be used, for example, as binders in paints and coatings. In addition, various additives, such as pigments, coalescing agents, rheology modifiers, fungicides, plasticizers, nitrates, and the like, may be added to the coatings. Paints with multi-functional acrylate binders may display high glass transition temperatures, and may be resistant to abrasion, and easily cure at room temperature. The coatings may generally be applied to any substrate such as, for example, an article, an object, a vehicle or a structure. Although no particular limitation is imposed on the substrate to be used in the present disclosure, examples of such substrates include, building exteriors, vehicles, bridges, airplanes, metal railings, fences, glasses, plastics, metals, ceramics, wood, stones, cement, fabric, paper, leather, and combinations or laminations thereof may be used. The coating may be applied to a substrate by, for example, spraying, dipping, rolling, brushing, or any combination thereof.

In some embodiments, the flame retardant compounds can be part of air entraining admixtures or agents. Air-entraining agents produce minute air bubbles on the order of 1.0 to 0.1 millimeters in diameter, that are uniformly distributed throughout a mixture of concrete and closed off from outside air so as to act as an additional "fine aggregate." In general, air-entraining agents include ethanol amine, diethanol amine, triethanol amine, dimethyl ethanol amine, methyl diethanol amine, tri-n-propanol amine, triisopropanol amine, isobutyl diethanol amine, n-butyl diethanol amine or mixtures thereof, and in some embodiments, the air-entraining agents may be salt-forming amino alcohols. In some embodiments, the rosin based flame retardants described above may act as air-entraining agents. For example, a rosin salt formed from a reaction between rosin and amine alcohol can function as an air entraining agent. Such rosin salts, when mixed and heated with aluminum sulfate can form flame retardant compounds.

Examples

Example 1: Preparation of a Flame Retardant

An alkaline solution was prepared with 0.5-2.0 g of sodium hydroxide (NaOH) in 20 mL of water. 1.5-3.0 g of Polyanhydride-18 (PA-18) was dissolved in 20 mL of the alkaline solution. 0.2-10 g of aluminum sulfate (Al2(SO4)3) was added to the alkaline PA-18 solution. The solution was heated for 15-30 min or until all the solvent evaporated to obtain the flame retardant product.

Example 2: Preparation of a Flame Retardant

An alkaline solution was prepared with 0.5-2.0 g of sodium hydroxide (NaOH) in 20 mL of water. 1.5-3.0 g of Airalon 3000 was dissolved in 20 mL of the alkaline solution. 0.2-10 g of aluminum sulfate (Al2(SO4)3) was added to the alkaline Airalon 3000 solution. The solution was heated for 15-30 min or until all the solvent evaporated to obtain the flame retardant product.

Example 3: Preparation of a Flame Retardant

An alkaline solution was prepared with 0.5-2.0 g of sodium hydroxide (NaOH) in 20 mL of water. 1.5-3.0 g of pyromelitic acid (PMA) was dissolved in 20 mL of the alkaline solution. 0.2-10 g of aluminum sulfate (Al2(SO4)3) was added to the alkaline PMA solution. The solution was heated for 15-30 min or until all the solvent evaporated to obtain the flame retardant product.

Example 4: Preparation of a Flame Retardant

In high intensity blender, 546.7 g of Airalon 3000 solution (an aqueous rosin resin solution), 1011.8 g of aluminum sulfate, and 107.7 g of expandable graphite were loaded. The ingredients were then blended for 15 minutes at to make the solution homogenous and drive off water. The solution produced was allowed to cool into a viscous solution or slurry.

Example 5: Preparation of a Flame Retardant

In a high intensity blender, 500.2 g of Bersize solution, 998.6 g of aluminum sulfate, and an 110.4 g of expandable graphite were loaded. The ingredients were then blended for 15 minutes to homogenize the solution and drive off water. The solution produced was allowed to cool into a viscous solution or slurry.

Example 6: Preparation of a Flame Retardant 250 g of flax seeds were loaded into 2 liters of boiling water. The flax seeds were then boiled for 15 minutes to extract mucilage from the seeds. 1 kg aluminum sulfate (Al2(SO4)3) was added and dissolved into the aqueous flax mucilage solution. These were mixed for 10 minutes to produce a homogenous mixture. The flax seeds were then strained from the solution. The solution was then boiled for 3 hours to reduce the volume and increase the solids mass percent. The solution was then poured into another container and solidified over the period of an hour. This solidified slurry having a paste-like consistency was dispensed into pans in 300 g aliquots and mixed with 12 g of expandable graphite. The paste and expandable graphite the mixture is heated with mixing for 10-15 minutes. The mixture is then left to cool and harden in the pan. The hardened paste is then ground into a powder.

Example 7: Preparation of a Flame Retardant

In a high intensity blender, 55.7 g of food-grade flour, 511.1 g of aluminum sulfate, 130.4 g of water and 35.3 g of expandable graphite were loaded. The ingredients were blended for 15 minutes at a high intensity to homogenize the solution and drive off water. The solution produced is then allowed to cool into a viscous solution or slurry.

Example 8: Preparation of a Flame Retardant

In a high intensity blender, 55.0 g of food-grade flour, 509.4 g of aluminum sulfate, and 34.5 g of expandable graphite were loaded. The ingredients were then dry blended at a high intensity to produce a homogenous powder.

Example 9: Preparation of a Flame Retardant

In a high intensity blender, 60.4 g of food-grade guar gum, 515.3 g of aluminum sulfate, 132.3 g of water, and 37.3 g of expandable graphite were loaded. The ingredients were then blended for 15 minutes at a high intensity to homogenize the solution and drive off water. The solution produced is then allowed to cool into a viscous solution or slurry.

Example 10: Preparation of a Flame Retardant

In a high intensity blender, 59.5 g of food-grade guar gum, 512.0 g of aluminum sulfate, and 36.7 g of expandable graphite were loaded. The ingredients were then dry blended at a high intensity to produce a homogenous powder.

Example 11: EN ISO 11925-2 Test

Test samples were produced by coating either expanded or unexpanded, expandable polystyrene beads with a flame retardant described in EXAMPLE 1-9. These samples were then processed to produce an expandable polystyrene board. The board produced is cut into 250×90 mm test samples having a thickness of 30-60 mm thick as required for the EN ISO 11925-2 test standards. Control test samples of expandable polystyrene board without any flame retardant coated onto the expandable polystyrene beads or exterior of the final board were also created.

EN ISO 11925-2 is a vertical flame test to measure the ignitability of building products when exposed to flame that is used as a guideline for construction products in Europe. Inside a test chamber, a test specimen is mounted vertically and exposed to a gas flame at an edge and/or on a surface. Time to ignition, burning droplets, and whether the flames reach the top marking of the test specimen within a prescribed time period are registered. The EN ISO 11925-2 results for EXAMPLES 1-9 are presented in TABLE 2:

TABLE II

| Flame Retardant | EN ISO 11925-2 Result | Performance Notes |
| --- | --- | --- |
| Example 1 | Fail | Improved flame retardancy over the control was observed. |
| Example 2 | Pass | |
| Example 3 | Fail | Improved flame retardancy over the control was observed. |
| Example 4 | Pass | |
| Example 5 | Pass | |
| Example 6 | Pass | |
| Example 7 | Pass | |
| Example 8 | Fail | Improved flame retardancy over the control was observed. |
| Example 9 | Pass | |
| Example 10 | Fail | Improved flame retardancy over the control was observed. |

What is claimed is:

1. A flame retardant compound of Formula I:

$$R^1\text{—}X\text{—}R^2 \qquad \text{I}$$

wherein:

the compound is a rosin compound, a polyanhydride compound, or combinations thereof and X is aryl, alkaryl, heteroaryl, cycloalkyl, heterocycloalkyl, cycloalkenyl, heterocycloalkenyl, polycyclic, or combinations thereof;

$R^1$ is a saturated aliphatic chain, an unsaturated aliphatic chain, a branched aliphatic chain, an unbranched aliphatic chain, a substituted aliphatic chain, a substituted aliphatic chain containing a halogen, an unsubstituted aliphatic chain, or any combination thereof; and $R^2$ is an oxidizable group selected from carboxyl, anhydride, amide, nitro, nitroso, thioester, and combinations thereof.

2. The compound of claim 1, wherein $R^1$ is an aliphatic chain having about 3 to about 22 carbon atoms.

3. The compound of claim 1, wherein $R^2$ is a carboxyl, an anhydride, an amide, or any combination thereof.

4. The compound of claim 1, wherein X is aryl, alkaryl, heteroaryl, cycloalkyl, heterocycloalkyl, or any combination thereof.

5. The compound of claim 1, further comprising a metal ion coordinated to one or more $R^2$ with the metal ion selected from the group consisting essentially of Fe, Al, Si, Ti, Zr, Hf, V, Nb, Ta, Cr, Mn, Mo, W, Re, Co, Ni, Cu and Group III metals.

6. A flame retardant compound of Formula II:

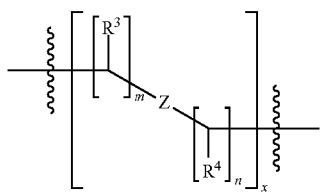

wherein:
m is an integer from 1 to 20;
n is an integer from 1 to 20;
x is an integer from 1 to 10,000;
each $R^3$ is individually a saturated aliphatic chain, an unsaturated aliphatic chain, a branched aliphatic chain, an unbranched aliphatic chain, a substituted aliphatic chain, an unsubstituted aliphatic chain, or any combination thereof;
each $R^4$ is individually an oxidizable group selected from a carboxyl, an anhydride, an amide, a nitro group, a nitroso group, a thioester group, and any combination thereof; and
Z is 0-20 atoms of carbon, oxygen, sulfur, phosphorous, and any combination thereof.

7. The compound of claim 6, wherein the compound is a rosin compound, a polyanhydride compound, or combinations thereof.

8. The compound of claim 6, wherein the compound is a bio-sourced material.

9. The compound of claim 8, wherein the bio-based materials bio-sourced material is a polysaccharide with associated or chemically bonded proteins having one or more ether, alcohol, epoxide, ketone, aldehyde, carboxylic acid, ester, acid chloride, amine, amide, imine, thioester, sulfone, thiol, sulfide, phosphate, phosphate ester, acyl phosphate, alkyl, alkene, alkyne, or combinations thereof.

10. The compound of claim 6, further comprising a metal ion coordinated to one or more $R^4$.

11. The compound of claim 6, wherein the compound is selected from:

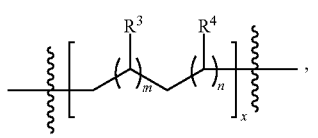

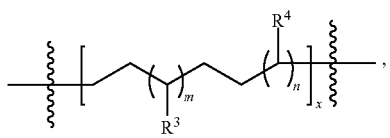

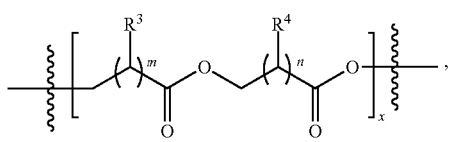

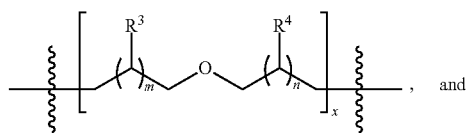

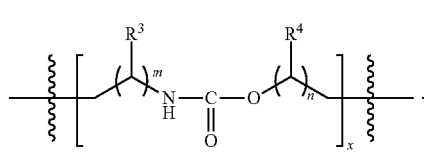

12. The compound of claim 11, further comprising a metal ion coordinated to one or more $R^4$.

13. A flame retardant compound of formula III:

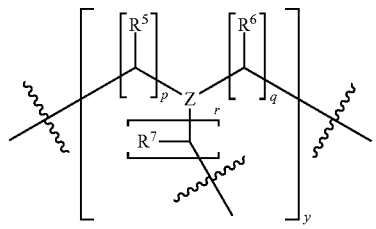

wherein p is an integer from 1 to 20;
q is an integer from 1 to 20;
r is an integer from 1 to 20;
y is an integer from 1 to 10,000;
each $R^5$, $R^6$, and $R^7$ is individually an aliphatic chain selected from a saturated aliphatic chain, an unsaturated aliphatic chain, a branched aliphatic chain, an unbranched aliphatic chain, a substituted aliphatic chain, an unsubstituted aliphatic chain, or any combination thereof;
each $R^5$, $R^6$, and $R^7$ is individually an oxidizable functional group selected from a carboxyl, an anhydride, an amide, a nitro group, a nitroso group, a thioester group, and any combination thereof; and
Z is 0-20 atoms of carbon, oxygen, sulfur, phosphorous, and any combination thereof, and
at least one of $R^5$, $R^6$, and $R^7$ is an aliphatic chain, and at least one of $R^5$, $R^6$, and $R^7$ is an oxidizable group.

14. The compound of claim 13, wherein the compound is a bio-sourced material.

15. The compound of claim 14, wherein the bio-sourced material is a polysaccharide with associated or chemically bonded proteins having one or more ether, alcohol, epoxide, ketone, aldehyde, carboxylic acid, ester, acid chloride, amine, amide, imine, thioester, sulfone, thiol, sulfide, phosphate, phosphate ester, acyl phosphate, alkyl, alkene, alkyne, or combinations thereof.

16. The compound of claim 13, further comprising a metal ion coordinated to at least one of $R^5$, $R^6$, and $R^7$ containing an oxidizable group.

17. The compound of claim 13, wherein the compound is selected from:
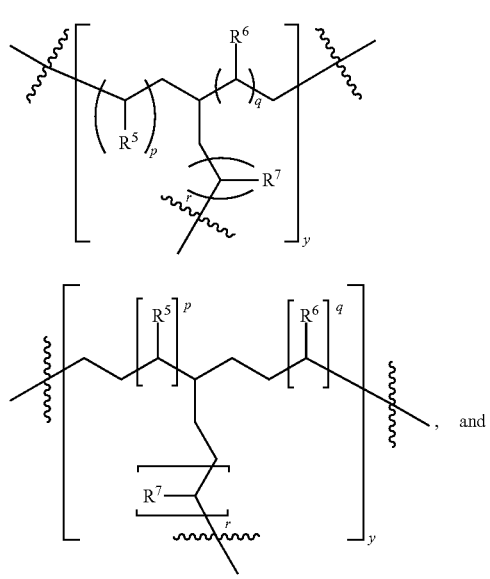
IIIa
IIIb
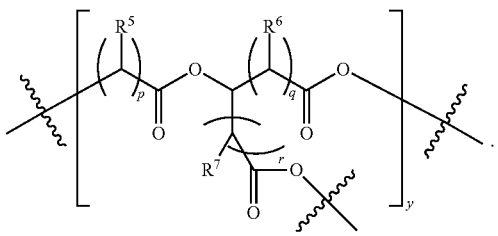
IIIc
18. The compound of claim 17, further comprising a metal ion coordinated to at least one of $R^5$, $R^6$, and $R^7$ containing an oxidizable group.
* * * * *